United States Patent [19]

Asano et al.

[11] 4,169,107

[45] Sep. 25, 1979

[54] PROCESS FOR MANUFACTURING AN AMIDE COMPOUND USING ALUMINUM NITRATE PROMOTER

[75] Inventors: Shiro Asano; Kiyotaka Yoshimura; Masao Hashimoto, all of Mobara, Japan

[73] Assignee: Mitsui Toatsu Chemicals, Incorporated, Tokyo, Japan

[21] Appl. No.: 838,368

[22] Filed: Sep. 30, 1977

Related U.S. Application Data

[63] Continuation-in-part of Ser. No. 474,786, May 30, 1974, abandoned.

[51] Int. Cl.$^2$ .................................................. C07C 102/08
[52] U.S. Cl. .............................. 260/561 N; 252/438; 252/477 Q
[58] Field of Search .................. 260/561 N; 252/438, 252/477 Q

[56] References Cited

U.S. PATENT DOCUMENTS

| | | | |
|---|---|---|---|
| 1,916,249 | 7/1933 | Barker | 252/474 X |
| 3,418,258 | 12/1968 | Ackermann et al. | 252/477 Q X |
| 3,544,485 | 12/1970 | Tiara et al. | 252/477 Q X |
| 3,869,511 | 3/1975 | Johnson et al. | 260/561 N |
| 3,911,009 | 10/1975 | Yoshimura et al. | 260/561 N |

*Primary Examiner*—Thomas Waltz
*Attorney, Agent, or Firm*—Fisher, Christen and Sabol

[57] ABSTRACT

An improved process for converting acrylonitrile to the corresponding amide by hydrating said nitrile in the presence of a metallic copper catalyst and aluminum nitrate as promoter for said catalyst.

3 Claims, No Drawings

4,169,107

PROCESS FOR MANUFACTURING AN AMIDE COMPOUND USING ALUMINUM NITRATE PROMOTER

CROSS REFERENCE TO RELATED APPLICATION

This application is a continuation-in-part of application Ser. No. 474,786 filed May 30, 1974, now abandoned.

BACKGROUND OF THE INVENTION

1. Field of the Invention

The present invention relates to a process for manufacturing an amide compound. More particularly, the present invention relates to converting acrylonitrile to acrylamide by hydrating acrylonitrile in the presence of a metallic copper catalyst and a promoter therefor.

2. Description of the Prior Art

Known processes for the conversion of a nitrile, e.g. acrylonitrile and the like, to the corresponding amide, e.g. acrylamide and the like, by hydrating the nitrile in the presence of a metallic copper catalyst include, for example, those disclosed in U.S. Pat. No. 3,631,104 and Belgian Pat. No. 753,365, the latter corresponding to copending U.S. application Ser. No. 56,967, filed July 21, 1970, now U.S. Pat. No. 4,056,565. The catalysts employed in these processes are metallic copper catalysts having a comparatively large surface area such as reduced copper, Raney copper, Ullmann copper, etc., obtainable by the application of the respective reducing processes specifically developed therefor. In spite of the effectiveness of such metallic copper catalysts in converting nitriles to the corresponding amides, it has been desired to improve the catalytic effects thereof when using them on an industrial scale.

One process proposed for improving the conversion rate of nitrile to amide when using a metallic copper catalyst comprises adding a cupric salt of an inorganic acid, e.g. copper nitrate, or the cupric salt of a fatty acid, e.g. copper acetate, to the reaction mixture as a promoter for the metallic copper catalyst. This process is described in U.S. Pat. Nos. 3,911,009 and 3,962,333. It is shown therein that the conversion rate to the amide is increased by as much as 70% when using the metallic copper catalyst in conjunction with the cupric salt promoter, whereas the increase in the conversion rate when using a metallic copper catalyst alone without the promoter is only 50%. However, it is still desirable when operating on a commercial scale that a promoter be found which will increase the rate of conversion from nitrile to amide and also maintain the catalytic life of the metallic copper catalyst for longer periods of time.

In U.S. Pat. No. 3,869,511 certain anions are disclosed as promoters for solid catalysts which contain elemental copper in the catalytic hydration of acrylonitrile with water to acrylamide. Chloride is the anion most preferred by the patentees. However, bromide, nitrate, and nitrite are also disclosed as significantly improving the activity of the copper catalysts. The effective anion is introduced into the reaction solution as a water soluble salt of the effective anion. The patentees state that the cations of the salts appear to be inert with respect to any improvement of catalyst activity and almost any soluble salt of the selected anion can be selected. The alkali metal and alkaline earth metal salts are said to be suitable and the sodium salts are preferred for their economy.

In the prior art processes, the type of reactor employed depends on the shape of the metallic copper catalyst. For example, if the catalyst is metallic copper which is obtained by reducing copper oxide with hydrogen, a fixed bed reactor which is filled up with the tablet-shaped catalyst may be employed. If the catalyst is metallic copper which is obtained by: (a) dissolving out a part of a Raney alloy or, (b) reduction-crystallization from an aqueous solution of copper salt, a fluidized bed reactor may be employed, in which the catalyst used is suspended in a liquid medium.

In the aforesaid reaction systems, upon separation of the catalyst particles from the reaction product-containing solution, the pulverized catalyst which fills up a reactor and the fine particles in a suspension often pose a problem in handling. Namely, in the aforesaid catalyst systems composed of a metallic copper catalyst and a catalyst promoter problems arise during the separation of the metallic copper catalyst from the reaction solution. When separating by sedimentation, low settling rates are obtained. When separating by filtration, high pressure drops across the filter result.

SUMMARY OF THE INVENTION

It is therefore an object of the present invention to provide an improved catalyst system for use in a process for hydrating acrylonitrile to the corresponding acrylamide.

It is another object of the present invention to provide such an improved catalyst system containing a promoter which will increase the speed of the hydration reaction of the acrylonitrile and also maintain the catalytic life of the metallic copper catalyst for long periods of time whereby the economic value of the hydration process is greatly improved.

It is a further object of the present invention to obtain a high conversion of acrylonitrile to acrylamide while simultaneously facilitating the separation of metallic copper catalyst from the reaction solution.

Still further objects and the entire scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description. It has been found that the above objects can be attained by practicing the present invention.

It has been found that the above objects can be attained by the process of the present invention wherein acrylonitrile is reacted with water in the presence of a metallic copper catalyst, e.g. Raney copper, reduced copper, Ullmann copper or copper dust, and also in the presence of aluminum nitrate as a promoter for the catalyst. The aluminum nitrate is used in an amount of from 1 to 600 ppm, preferably 3 to 200 ppm, calculated as the weight proportion (ratio) of the nitrate ion to the gross weight of the mixture of nitrile and water. In the process of the present invention, acrylamide is manufactured at a high rate of yield and the catalyst remains completely free of factors which would tend to decrease catalytic activity or shorten the effective life of the metallic copper catalyst. In addition, the catalyst is easily separated from the reaction solution.

No other catalyst promoter has been found which gives both the high conversion rates and ease of separation of copper catalyst by settling or filtering as obtained with the aluminum nitrate promoter of the present invention.

DESCRIPTION OF THE PREFERRED EMBODIMENTS

Addition of aluminum to the reaction system may be accomplished by dissolving aluminum nitrate in the water or acrylonitrile reactant. Alternatively, aluminum nitrate may be separately dissolved and then added into the reactor or the circulation system of the reaction liquid.

The quantity of aluminum nitrate added to the reaction mixture is within the range of from 1 to 600 ppm calculated and expressed as the weight ratio of the nitrate ion to the gross weight of the reaction mixture of nitrile and water. When the quantity of aluminum nitrate is less than 1 ppm, such a level has an unsatisfactory promoter effect. When the quantity of promoter is in excess of 600 ppm, there is a tendency that the long term activity of the metallic copper catalyst may be adversely affected, compared with the catalytic activity when no promoter is added, even though a temporary improvement of activity of the catalyst can still be observed. Optimum increases in catalytic activity and effective catalyst life will occur when the amount of nitrate added is within the preferred range of from 3 to 200 ppm.

The metallic copper catalyst which may be employed in the process of the present invention is one which contains metallic copper as the major effective constituent of the cayalyst. Suitable metallic copper catalysts which are illustrative but not limiting are:

(1) Copper dust prepared (ground) from a metallic copper ingot, a microfine piece of copper wire, and the like;

(2) Reduced copper such as is obtained through reduction of a copper compound such as copper oxide, copper hydroxide, copper chloride and the like, conducted by the employment of hydrogen and/or carbon monoxide in a temperature range of 0°–500° C.;

(3) Reduced copper such as is obtained through reduction of a copper compound such as copper oxide, copper hydroxide, copper chloride and the like, conducted by the employment of a conventional reducing agent such as hydrazine, sodium borohydride and the like, in the liquid phase;

(4) Reduced copper such as is obtained through treatment of a copper compound such as copper oxide, copper hydroxide, copper chloride and the like, conducted by the employment of a metal which has a higher ionization tendency than copper, such as zinc, aluminum, iron, tin, and the like, in the liquid phase;

(5) Raney copper such as is obtained through proper development of a Raney alloy comprising copper and aluminum, zinc, or magnesium;

(6) Such copper as is obtained through subjecting a copper compound such as formate or oxalate to thermal cracking at a temperature range of, for example, 100°–400° C.;

(7) A multielement catalyst as is obtained by combining another metal such as chromium, zinc, nickel, manganese or molybdenum with one of the foregoing copper metal substances during preparation of the catalyst therefrom; and (8) Any of the above catalysts supported on a carrier of an essentially inert material such as alumina, silica, Kieselguhr, pumice, diatomaceous earth, etc. such as prepared by depositing the catalyst on the inert carrier during preparation thereof.

One suitable method for preparing a Raney copper catalyst is the Raney technique, similar to that normally associated with preparing Raney nickel. Commercial formulations for use in preparing these catalysts are readily available, e.g. an alloy of aluminum and copper. The catalysts are developed or activated by known techniques to give the metallic copper catalyst suitable for use in the process of the present invention. Normally such techniques involve contacting the alloy with a strong base under conditions which leach out the aluminum or other metal.

The difference of the above-described catalysts lie not so much in the selectivity of the reaction thereof as in the intensity of the activity thereof. When acrylonitrile is subjected to a hydration reaction under such conventional reaction conditions as will be more fully described hereinafter, by making a proper selection of the foregoing catalysts and by preparing the catalysts to have exceptional purity, the reaction selectivity factor for acrylamide is 97% or higher and the reaction selectivity factor for ethylene cyanohydrin is 2% or less.

The quantity of metallic copper catalyst preferably employed in the process of the present invention is within the range of from 0.01 to 1,000 grams per mol of nitrile when, for example, subjecting the reaction mixture to the metallic copper catalyst in a suspension bed thereof. The metallic copper catalysts of the present invention are convenient for use in both a batch process and a continuous flow process. Using either method, the nitrile and water are contacted with the catalyst under appropriate reaction conditions and the amide product is then recovered.

The proportions of nitrile to water in the reaction mixture may vary widely since any amount of water that gives the hydration is acceptable. More important than the acrylonitrile to water ratio is the extent of interaction between the reactants. A high degree of contact is desirable to assure greatest efficiency. For liquid reactants, certain measures may be helpful to insure that intimate contact of acrylonitrile and water is maintained, e.g. dissolving acrylonitrile in the water or dissolving the water in the acrylonitrile. Outside the limits of solubility of one reactant in the other, the reaction mixture may be agitated, a suitable compatible solvent may be added or other means may be employed. Suitable inert compatible solvents include alkanols such as methanol, dioxane, dimethyl sulfoxide, acetone, dimethyl ether of ethylene glycol, tetrahydrofuran, etc. The recommended ratio of nitrile to water is generally one wherein the weight of the water is in excess of the weight of the nitrile compound, e.g. using water in a range of from 50 to 90 weight percent of the reaction mixture.

Generally, the reaction is conducted within a temperature range of from about 50° to 400° C. At temperatures below this level the reaction is impractically slow and above this range an increasing amount of undesirable by-products may be formed. The preferred temperature is within the range of from 50° to 300° C. An even more preferred temperature range for avoiding side reactions and polymerization in the conversion of acrylonitrile to acrylamide is from 50° to 150° C.

The reaction solution obtained by reacting under the aforesaid conditions contains relatively fine catalyst particles. However, the size of the catalyst particles varies depending on the type of reactor employed. These catalyst particles are generally separated from the reaction solution in or out of the reactor by filtration or, a combination of sedimentation and filtration. The objective of the separation is to obtain a reaction solution which does not contain catalyst particles.

Hitherto, it has not been easy to separate the catalyst particles from the reaction solution. For instance, there are many difficulties associated with the separation such as long sedimentation-and-filtration time, pressure loss upon filtration, incomplete filtration of catalyst particles, and the like.

A known continuous separation process for the catalyst particles employs a reactor which has a settling separator and a filter. In this continuous process, the catalyst particles are accumulated on the filter with the progress of the operation and a pressure loss across the filter increases along with the accumulation. It is therefore necessary to either replace the filter with a spare filter or to interrupt the continuous operation to clean the filter when the maximum permitted pressure loss is reached.

The number of days of operation before reaching the maximum permissible pressure loss increases in proportion to the filterability of the catalyst. Where aluminium nitrate is employed as the promoter as in the present invention, the number of days of operation before reaching the maximum pressure loss is extremely remarkable. For instance, the number of days of continuous operation is twice as long as the conventional case where copper nitrate is employed.

In the case where the operation of the process is continued while the filter is changed with a spare one, the employment of aluminium nitrate as a catalyst promoter improves filterability so that the time required for replacement of the filter reaches up to several months. The employment of aluminium nitrate achieves a high level of conversion of acrylonitrile to acrylamide and at the same time enables easy separation of the metallic copper catalyst from the reaction solution.

The above-mentioned latter effect is even more remarkably seen with a reactor in which the metallic copper catalyst is in suspension rather than with a reactor which is filled up with the subject catalyst. The above difference between the two types of reactors is due to the fact that the reaction solution of the former case contains a larger amount of the catalyst than in the latter case. Greater filterability of the catalyst is therefore required in the former case.

The water solutions of the amide compounds obtained by the process of the present invention contain only negligible quantities of the aluminum nitrate employed herein and hence they are capable of being employed directly as intermediate materials. It is not necessary to subject the water solutions of the amide compounds to refining. It will be understood, however, that any ions which are added can be properly removed, whenever so required, for example, by the employment of an ion-exchange resin.

Furthermore, when the product is a water solution of acrylamide, the same can be employed as a water solution for obtaining such polymers as are useful as agents for paper processing or soil stabilization. Also, acrylamide crystals can be obtained from the water solution of acrylamide by a conventional process.

Another advantage obtainable by the process of the present invention lies in the fact that the life of the metallic copper catalyst employed for the manufacture of an amide compound from a nitrile compound can be considerably improved, whereby any amide compound can be manufactured on an industrial scale and in an efficient manner.

Described in more concrete terms, the proper combination of metallic copper catalyst and aluminum nitrate promoter according to the present invention, unlike the hitherto known combination of metallic copper catalyst with cupric salt promoter, can substantially prevent the activity of the catalyst from being subjected to deterioration and, as a result, the quantity of metallic copper catalyst consumed can be reduced, and the economical value of the process is thus enhanced.

The following examples are illustrative of but do not limit the process of the present invention. In the examples, all parts are parts by weight and all weights are dry weights unless otherwise indicated. In all of the tables, the amount of promoter in ppm is calculated and expressed as the weight ratio of the nitrate ion to the gross weight of the raw material liquid comprising nitrile and water.

EXAMPLE 1

1500 g of Raney copper were placed in a 10 liter reaction vessel equipped with a stirrer and provided with a catalyst separating zone therein. To a reaction solution outlet port of the reaction vessel was further connected a filter provided with a filtration cloth having a filtration area of 80 $cm^2$. Acrylonitrile and water, having had approximately 90% of dissolved oxygen removed in a deoxidizing apparatus were then continuously fed to the reaction vessel at rates of 3.0 kg/hour and 7.0 kg/hour, respectively, and the reaction was carried out at 120° C. The water had been previously mixed with aluminum nitrate -(9)-hydrate in an amount of 57 ppm. Thus, the concentration of nitrate ion in the reaction mixture (total amount of water and acrylonitrile) was 20 ppm. The reaction solution withdrawn from the outlet port was found to contain a trace amount of Raney copper particles, but, after passing through the filter, the solution was found to contain almost no Raney copper.

The reaction was continued for 30 days. During the reaction, conversion of acrylonitrile to acrylamide was examined several times. Also, the difference in the pressure between the upstream and downstream sides of the filter was measured by a pair of pressure gauges.

The above example was repeated with the use of copper nitrate instead of aluminum nitrate. The concentration of nitrate ion was the same as in the first experiment. In this second experiment, the difference in the pressure upstream and downstream of the filter increased from day to day and, after 20 days, it became impossible to continue the experiment.

The results of these experiments are as summarized in Table I:

Table I

| Day Measured | Conversion (%) | | Pressure Difference ($kg/cm^2$) | |
|---|---|---|---|---|
| | Aluminum Nitrate | Copper Nitrate | Aluminum Nitrate | Copper Nitrate |
| Commencement | 71 | 68 | 0.1 | 0.1 |
| after 5 days | 55 | 50 | 0.1 | 0.3 |
| after 10 days | 49 | 43 | 0.2 | 0.6 |
| after 15 days | 45 | 38 | 0.4 | 1.4 |

Table I-continued

| Day Measured | Conversion (%) | | Pressure Difference (kg/cm$^2$) | |
|---|---|---|---|---|
| | Aluminum Nitrate | Copper Nitrate | Aluminum Nitrate | Copper Nitrate |
| after 20 days | 43 | stop | 0.5 | stop |
| after 25 days | 40 | — | 0.8 | — |
| after 30 days | 39 | — | 1.0 | — |

As is evident from the table, the conversion of acrylonitrile to acrylamide unexpectedly ranges between 3% and 7% higher during the first fifteen days of operation when aluminum nitrate rather than copper nitrate is used as a promoter. In addition, after 20 days of operation, the pressure difference across the outlet filter was only 0.5 Kg/cm$^2$ with the aluminum nitrate promoter. Operation had to be halted with the copper nitrate promoter.

EXAMPLE 2

The procedure of Example 1 was repeated for 6 consecutive days with varying amounts of nitrate to provide from 4 ppm to 1,000 ppm of promoter in the reaction liquids. The results are shown in Table 2:

Table 2

| Day of analysis | Factors of conversion (%) | | | | | |
|---|---|---|---|---|---|---|
| | No promoter added | nitrate ion added (ppm) | | | | |
| | | 4 | 20 | 100 | 400 | 1,000 |
| Initial day | 51 | 59 | 70 | 69 | 64 | 61 |
| after 2 days | 42 | 51 | 64 | 62 | 50 | 13 |
| after 4 days | 37 | 46 | 59 | 56 | 42 | 6 |
| after 6 days | 33 | 41 | 56 | 52 | 38 | 2 |

EXAMPLE 3

300 grams of copper oxide tablets were placed so as to fill a metal reaction pipe having a volume of 300 cc. and were reduced thoroughly into reduced copper metal at a temperature of 200°–250° C. using hydrogen gas diluted to 2% with nitrogen. The reaction pipe was supplied, in a continuous manner, with water and acrylonitrile having had approximately 90% of dissolved oxygen previously removed therefrom by passing the same through a deoxidizing apparatus, at rates of 700 grams/hour and 300 grams/hour, respectively. The mixture in the reaction pipe was then subjected to reaction at a temperature of 120° C. The water originally contained 39 ppm of aluminum nitrate and this corresponded to 20 ppm of promotor in the reaction mixture containing both acrylonitrile and water. The results of the reaction were observed for 6 consecutive days and are shown in Table 3. An additional experiment was conducted with no aluminum nitrate added for comparison purposes.

TABLE 3

| Day of Analysis | Factors of conversion (%) | |
|---|---|---|
| | Nitrate ion (ppm) | No promoter added |
| Initial day | 76 | 49 |
| after 2 days | 68 | 43 |
| after 4 days | 63 | 38 |
| after 6 days | 59 | 35 |

Similar experiments were conducted using a catalyst as was obtained through reduction of a cupric salt, as well as a copper-chromium oxide catalyst which was subjected to a hydrogen reduction treatment by the employment of hydrazine. The results of the said experiments were virtually the same as those shown in Table 3.

What is claimed is:

1. In a process for preparing acrylamide by reacting acrylonitrile with water at a temperature of from 50° to 400° C. in the presence of a metallic copper catalyst and a promotor thereof, the improvement comprising using aluminium nitrate as said promotor in an amount of 3 to 600 ppm by weight of the nitrate ion to the total amount of the acrylonitrile and water in the reaction mixture.

2. A process according to claim 1, wherein said nitrate ion is present in the range of 3 to 200 ppm.

3. A process according to claim 1, wherein said metallic copper catalyst is present in suspension in a reactor.

* * * * *